United States Patent [19]
Mani et al.

[11] Patent Number: 5,588,431
[45] Date of Patent: Dec. 31, 1996

[54] INVERSION RECOVERY MRI

[75] Inventors: Sanjay Mani; Dwight G. Nishimura, both of Palo Alto; Steven M. Conolly, Menlo Park; John M. Pauly, San Francisco, all of Calif.

[73] Assignee: The Board of Trustees of the Leland Stanford Junior University, Palo Alto, Calif.

[21] Appl. No.: 516,243

[22] Filed: Aug. 17, 1995

[51] Int. Cl.$^6$ .................................................. A61B 5/055
[52] U.S. Cl. ............................. 128/653.3; 128/653.1; 128/653.2; 324/307; 324/309; 324/312
[58] Field of Search .............................. 128/653.1, 653.2, 128/653.3; 324/307, 309, 312

[56] References Cited

PUBLICATIONS

Coronary Angiography with Magnetization–Prepared $T_2$ Contrast Brittain et al., May 1995 vol. 33; No. 5 Magnetic Resonance in Medicine.

*Primary Examiner*—Marvin M. Lateef
*Assistant Examiner*—Eleni Mantis Mercader
*Attorney, Agent, or Firm*—Townsend and Townsend and Crew LLP

[57] ABSTRACT

Multiple inversion recovery flow imaging employs at least four spin inversion pulses following saturation of static nuclei spins to null nuclei in static material having different spin-lattice relaxation times ($T_1$) with the inversion pulses being spaced in time to substantially reduce the longitudinal magnetization of the $T_1$ species present. The saturation of static nuclei spins includes applying a sequence of saturation pulses with adjacent pulses being separated by a diphasing gradient to avoid refocusing coherence. The detection of signals includes applying at least one RF read-out pulse near the nulling point.

12 Claims, 6 Drawing Sheets

INVERSION RECOVERY MRI

This invention was made with U.S. Government support under grant No. NS 29434 awarded to Stanford University by the National Institute of Health. The Government has certain rights in this invention.

BACKGROUND OF THE INVENTION

This invention relates generally to magnetic resonance imaging (MRI) and, more particularly, the invention relates to multiple inversion recovery imaging.

Magnetic resonance imaging (MRI) is a non-destructive method for the analysis of materials and represents a new approach to medical imaging. It is generally non-invasive and does not involve ionizing radiation. In very general terms, nuclear magnetic moments are excited at specific spin precession frequencies which are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

Multiple inversion recovery (MIR) for selectively imaging blood grew out of the SIR (Selective Inversion Recovery) technique introduced by Nishimura et al., MRM, 4, 193–202 (1987). In SIR the blood upstream of the imaging region is inverted, and then after an inflow time a projection is made of this imaging region, into which the inverted blood has flowed. The positioning is made of this imaging region, into which the inverted blood has flowed. The positioning of these pulses is displayed in FIG. 3A. A projection is subsequently made of the imaging region without inverting the inflowing blood, and the projections are subtracted. The sequence thus produces an image of the blood that has flown into a large slab during some inflow time.

SIR has several advantages over competing time-of-flight techniques, notably that there is no nonlinear MIP projection imposed upon the data, which can cause mistaken estimation of stenosis. In addition, tortuous vessels are accurately imaged, and the sequence is easily gated, avoiding pulsatile flow artifacts which are also accentuated around stenosis.

However, there are several problems with SIR, each frame of data requires two excitations, and the subtraction can cause misregistration artifacts due to the large static signal. To reduce this large static signal, Dixon et al., MRM, 18, 257–268 (1991), proposed doing multiple inversions before acquisition, and also proposed doing the imaging in a non-subtractive fashion if the suppression was adequate. Dixon et al. demonstrated a non-subtractive image of the carotids using 2 inversions. Non-subtractive inflow imaging avoids misregistration problems, and allows image formation in half the excitations of SIR. Dixon et al. first saturated a slab and then performed 2 inversions, which should null (i.e., substantially reduce the longitudinal magnetization) muscle and fat after an inflow time. A projection was then taken of the slab, which should only display the blood that has flowed in to the slab since the saturation. However, imperfections in the multiple inversion technique due to various inhomogeneities can cause inaccurate background nulling. As blood is often only 1/20 of the tissue signal, even allowing 5% of the signal background to remain creates a signal-to-noise ratio of 1:1 when projecting through a slab.

The present invention remedies the difficulties in performing non-subtractive angiograms, providing robust static tissue suppression in human patients on the order of 60 dB. This allows consistent and easy imaging of vessels and their stenoses in various regions of strong flow, such as the carotid and renal arteries.

SUMMARY OF THE INVENTION

In accordance with the invention, after applying RF excitation to saturate static nuclei spins in an object to be imaged, at least four spin inversion pulses are applied to null nuclei in static material having different spin-lattice relaxation times ($T_1$). The spin inversion pulses are timed to null the longitudinal magnetization of various $T_1$ species after an inflow time.

In a preferred embodiment, a sequence of saturation pulses is applied with adjacent pulses being separated by a dephasing gradient to avoid refocusing coherence. In detecting the resulting magnetic resonance signals, a plurality of RF read-out pulses is applied with each pulse being followed by an inversion pulse, the detecting of emitted signals occurring between an RF read-out pulse and an inversion pulse.

The sequence produces static longitudinal magnetization suppression on the order of background noise. This allows non-subtractive projection images of regions of strong flow, such as the carotids, to be taken with clear visualization of the vessels of interest.

The invention and objects and features thereof will be more readily apparent from the following description and appended claims when taken with the drawings.

DETAILED DESCRIPTION OF ILLUSTRATIVE EMBODIMENTS

Figure 1A:
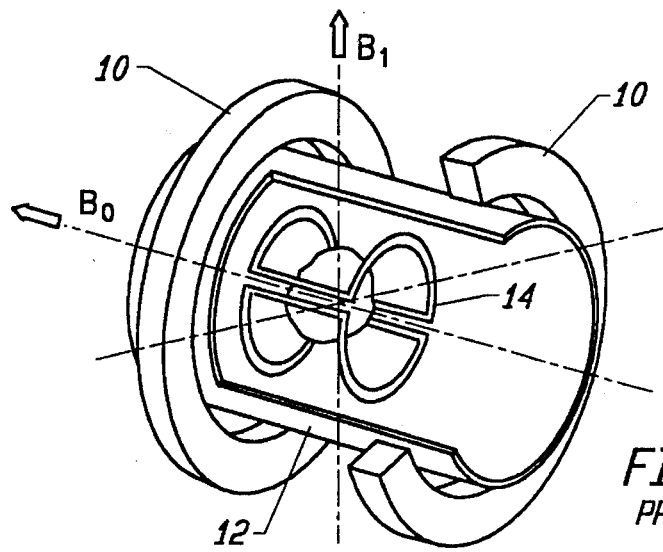
FIGS. 1A–1D illustrate the arrangement of conventional MRI apparatus and magnetic fields generated therein.
Figure 1B:
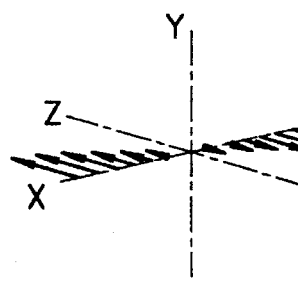
Figure 1C:
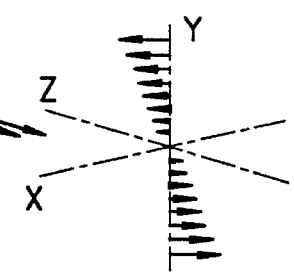
Figure 1D:
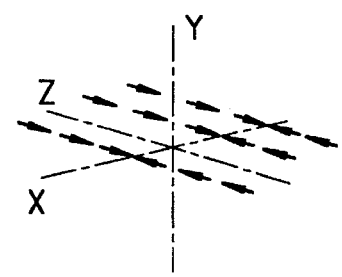

Referring now to the drawings, FIG. 1A is a perspective view partially in section illustrating coil apparatus in an NMR imaging system, and FIGS. 1B–1D illustrate field gradients which can be produced in the apparatus of FIG. 1A. This apparatus is discussed by Hinshaw and Lent, "An Introduction to NMR Imaging: From the Bloch Equation to the Imaging Equation," Proceedings of the IEEE, Vol. 71, No. 3, March 1983, pp. 338–350. Briefly, the uniform static field $B_0$ is generated by the magnet comprising the coil pair 10. A gradient field $G_x$ is generated by a complex gradient coil set which can be wound on the cylinder 12. An RF field $B_1$ is generated by a saddle coil 14. A patient undergoing imaging would be positioned along the Z axis within the saddle coil 14.

In FIG. 1B an X gradient field is shown which is parallel to the static field $B_0$ and varies linearly with distance along the X axis but does not vary with distance along the Y and Z axes. FIGS. 1C and 1D are similar representations of the Y gradient and Z gradient fields, respectively.

Figure 2:
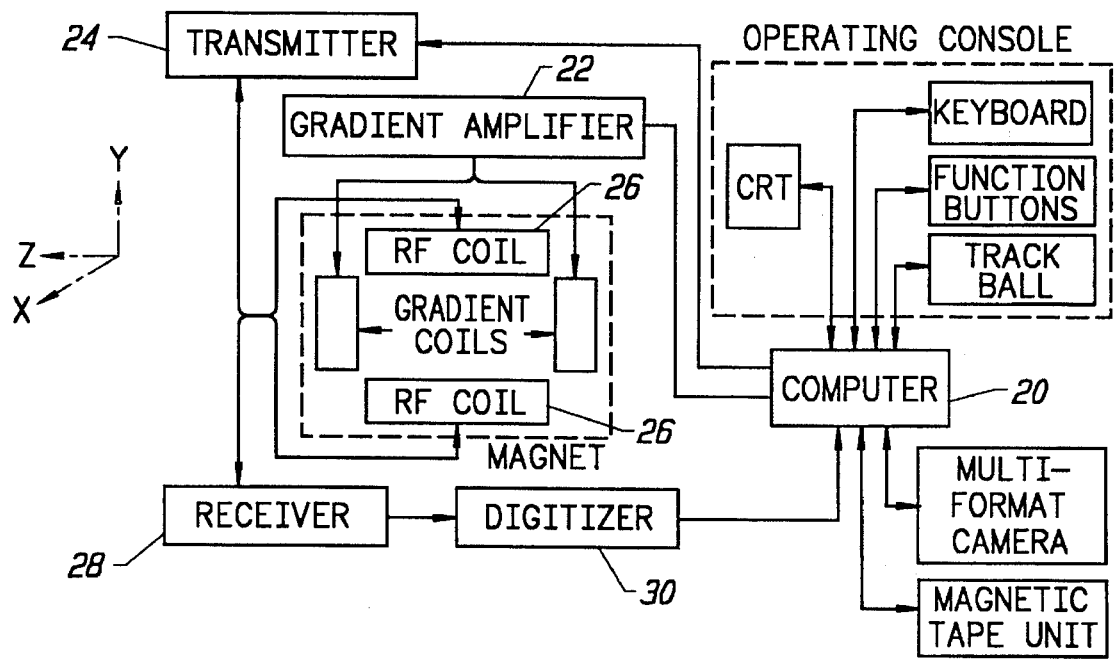
FIG. 2 is a functional block diagram of MRI imaging.

FIG. 2 is a functional block diagram of the imaging apparatus as disclosed in *NMR—A Perspective on Imaging*, General Electric Company. A computer 20 is programmed to control the operation of the NMR apparatus and process free induction decay (FID) signals detected therefrom. The gradient field is energized by a gradient amplifier 22, and the RF coils for impressing an RF magnetic moment at the Larmor frequency is controlled by the transmitter 24 and the RF coils 26. After the selected nuclei have been flipped, the RF coils 26 are employed to detect the FID signal which is passed to the receiver 28 and then through digitizer 30 for processing by computer 20.

As noted above, an MR angiogram is an image of the blood in a region of the body. In multiple inversion recovery imaging, an image is made of the blood that flows into a large slab. For example, a projection angiogram could be performed on the carotid arteries in the neck, or a slice angiogram could be made of perfusing blood in the brain cortex. MIR exploits the longitudinal relaxation properties of tissue, in that each tissue relaxes exponentially with a characteristic recovery time known as $T_1$. Different tissues relax with different values of $T_1$. If a spatial region is first saturated, meaning its longitudinal magnetization ($M_z$) is equal to 0, and then timed inversions are performed upon it, the final $M_z$ is $$M_z = 1 + \sum_{i=1}^{n} (-1)^i 2 \exp(-\tau_i/T_{1j}) + (-1)^{n+1} \exp(-Q/T_{1j}) \quad (1)$$

Figures 3A, 3B:
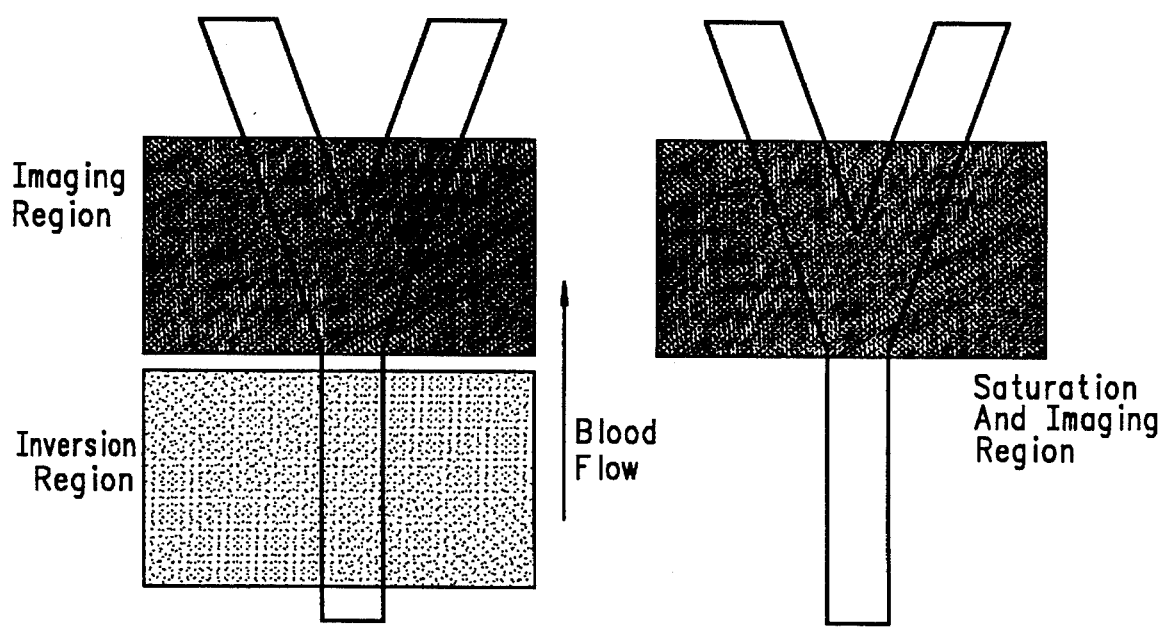
FIGS. 3A, 3B illustrate Selective Inversion Recovery and Multiple Inversion Recovery.
Figure 4:
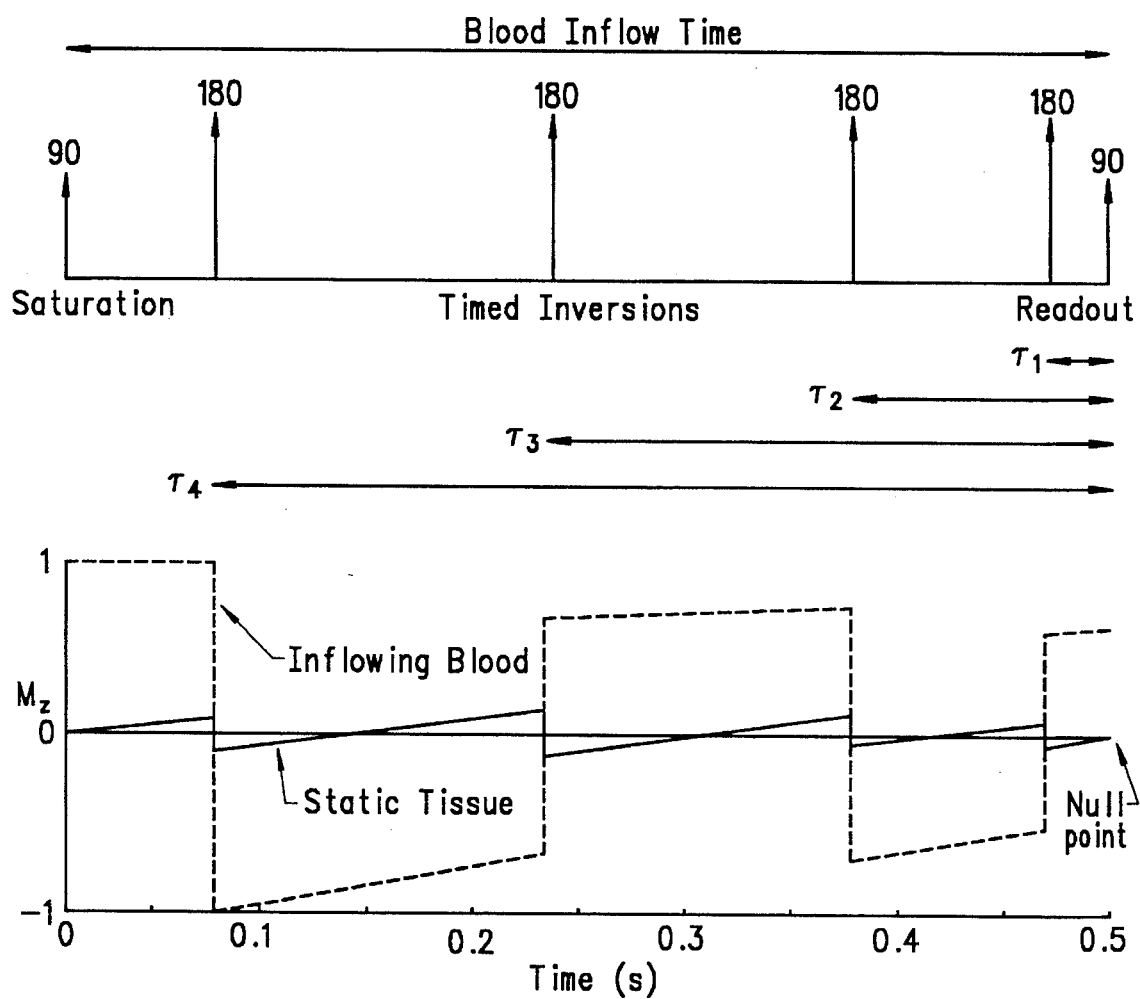
FIG. 4 illustrates the timing of a multiple inversion pulse sequence.

$M_z$=longitudinal magnetization
n=number of inversions
$\tau_i$=time from inversion i to null point
$T_{1j}$=$T_1$ of species j being nulled
Q=blood inflow time Equation (1) gives the final $M_z$ for a given $T_{1j}$ after n inversions spaced $\tau_i$ away from the nulling point. FIG. 3B displays the spatial orientation of the nulling sequence, while FIG. 4 displays the timing.

An MIR sequence is a saturation pulse, followed by n inversions timed to set $M_z$ for species with different $T_{1j}$ to zero after some inflow time Q. This point when the static tissue $M_z$ is zero will be described as the null point, so the null point is Q ms after the saturation pulse. Exciting at the null point will allow readout of only the blood that has flown into the region, as that alone has a non-zero $M_z$ at this point. To calculate the inversion timing, $M_z$ is set to zero in equation (1), and an inflow time and number of inversions is chosen. There are several optimization strategies that can then be used to find $\tau_i$, the times at which inversions should be played to produce the lowest final static tissue $M_z$.

Algebraically, with n inversions, n $T_{1j}$ species can be nulled, as this would be n equations with n unknowns. However, since the equations are nonlinear, the timing solution is found with an optimization strategy which need not be n equations with n unknowns. One can vary $\tau_i$ to minimize a weighted sum of squares of final $M_z$, using $T_{1j}$ for fat, muscle, and blood. The weighting can be for varying amounts of tissue, or can be uniform. It is also possible to minimize for a range of $T_1$. Different optimization algorithms with different starting points also yield varying sets of $\tau_i$ to minimize the final static tissue $M_z$, so care must be taken to choose good solutions.

There are several obvious applications to performing this inflow angiogram sequence, imaging blood vessels and therefore their stenosis being the clearest. Useful vessels to image are those with strong flow, such as the carotid, renal, and potentially coronal arteries. These vessels can be imaged in projection format, as all the static tissue surrounding them is being suppressed. In addition, this technique can be used to image perfusion, the slow flow of blood through the capillaries, by allowing long inflow times on the order of 1 to 2 seconds. In the strong flow regions, the imaging region is generally a projection perpendicular to the vessel to display the vessel. Hence the saturation pulse is limited along the vessel, as displayed in FIG. 3A. In a perfusion sequence, the projection would probably be made along the flow direction. In the brain, for example, this would allow axial slices to be imaged displaying slow flow in the axial direction.

In accordance with the invention the nulling process can robustly null to the order of background noise, primarily by using 4 inversions and pulses designed to overcome off-resonance and rf inhomogeneities. This sequence thus allows routing imaging of large slabs for inflow, as well as the imaging of slices for perfusion, without subtraction.

Figure 5:
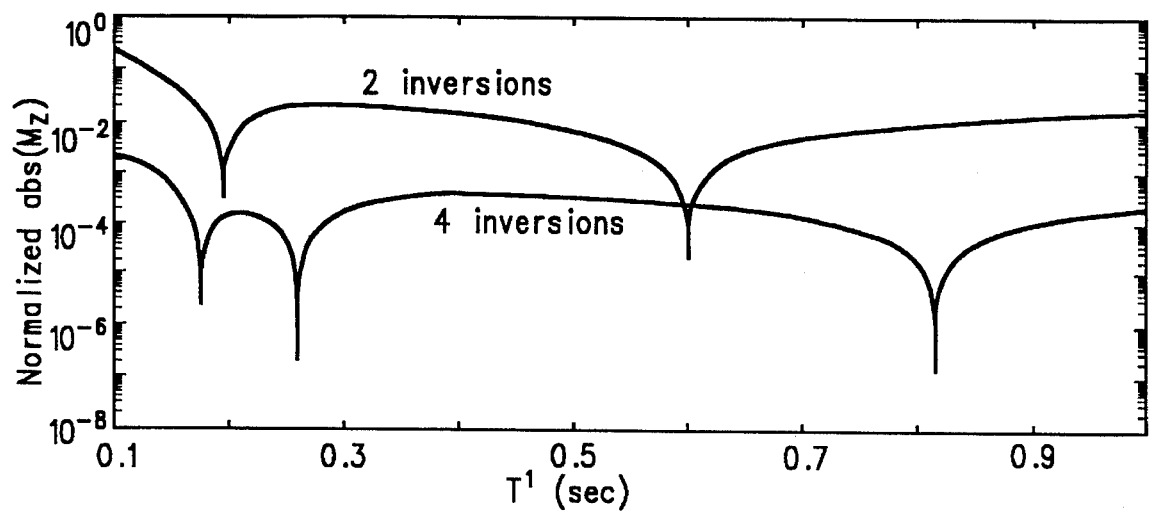
FIG. 5 illustrates a prior art two inversion sequence and four inversion sequence in accordance with the invention.

Each inversion can theoretically null one $T_1$ species. However, uncertainty in $T_1$ can hurt suppression. Four inversions can be timed to suppress a wide range of $T_1$, as seen in FIG. 5, avoiding timing optimization when imaging. Since using four inversions, as opposed to two, allows much more robust nulling and avoids continually improving timing for each case, it is an essential element in making this technique work consistently. With four inversions, species with $T_1$ varying from the ones that were optimized for are also suppressed, due to the wide range of suppression. The timing is generally determined by minimizing a non-weighted sum of squares of final $M_z$, using $T_{1j}$ for fat, muscle, and blood. Various starting points are used for the minimization algorithm, and the solution with the best minimization over a wide range of $T_1$ is chosen.

Four inversions were used for this sequence because each of the adiabatic sech inversions has high SAR (power deposition). However, given the robust nulling of four inversions, there may be tradeoffs using more inversions each having lower SAR. Error in each inversion would be compensated by increasing the total number of inversions.

Error in each inversion and the saturation, due to spatially varying rf strength (B1 inhomogeneity) or off-resonance, will cause imperfect nulling. These errors will cause incorrect tip angles, so that the $M_z$ of the static tissue at the null point will not be suppressed enough.

In the inversions, these problems are overcome by using wide bandwidth adiabatic sech inversions. See Conolly et al., JMR, 83, 549–564 (1989). Since the inversions are played with no gradients, the wide bandwidth inverts a large range of off-resonance and the adiabatic character of the pulses makes them very insensitive to rf variations.

Figure 6:
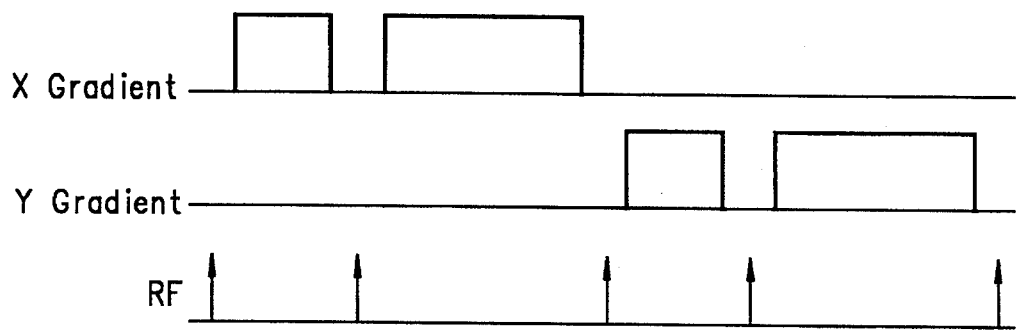
FIG. 6 illustrates a saturation sequence in accordance with an embodiment of the invention.

For the saturation, a pulse sequence similar to CHESS sequence used in MR spectroscopy is used. See Moonen et al., JMR, 88, 28–41 (1987). A sequence of five saturation pulses, each pulse separated by a dephasing gradient selected to avoid refocussing coherence, produces robust saturation despite B1 inhomogeneity. This provides saturation on the order of $[\cos(\theta)]^5$ where $\theta$=tip angle. The sequence is illustrated in FIG. 6.

Figure 7A:
FIGS. 7A–7D are MIR projections obtained in accordance with the invention.
Figure 7B:
Figure 7C:
Figure 7D:

This sequence was implemented on a stock 1.5T GE Signa system. Representative projections are displayed in FIG. 7A, FIG. 7B and FIG. 7C, 3 2DFT readout images of the carotids, and FIG. 7D one spiral image of the renals. The top two carotid images were acquired in 2 min, the carotid image on the lower left was acquired in 4 min, and the renal image was acquired in 1 min 20 sec. All images are using a 400 ms inflow time. The SAR of this sequence is 0.84 watts/kg. Unsuppressed static tissue signal is on the order of background noise, as is visible in FIG. A, FIG. B, FIG. C and FIG. D.

A B1 inhomogeneity resistant saturation sequence followed by four adiabatic inversions produces static suppression on the order of the background noise. This allows non-subtractive projection images of regions of strong flow, such as the carotids, to be taken with clear visualization of the vessels of interest. Other candidates for imaging are the renal vessels and the coronary vessels. In addition, this sequence can be combined with various readout techniques, including segmented k-space acquisition, fast spin echo, spiral readout, echo-planar readout, and standard 2DFT. Spiral and 2DFT readouts have already been implemented.

Generally in regions of strong flow, the sequence is implemented in a gated fashion to reduce pulsatile flow artifacts and provide consistent inflow for each acquisition. However, flow compensating gradients can be used to reduce flow artifacts, potentially allowing ungated imaging.

Since there is one null point, a multi-tip readout would be implemented by acquiring the low-frequency k-space values near the null, and the higher frequency k-space values away from the null. Although the higher frequency values would have imperfect suppression, only high-frequency static structures would remain.

Figure 8:
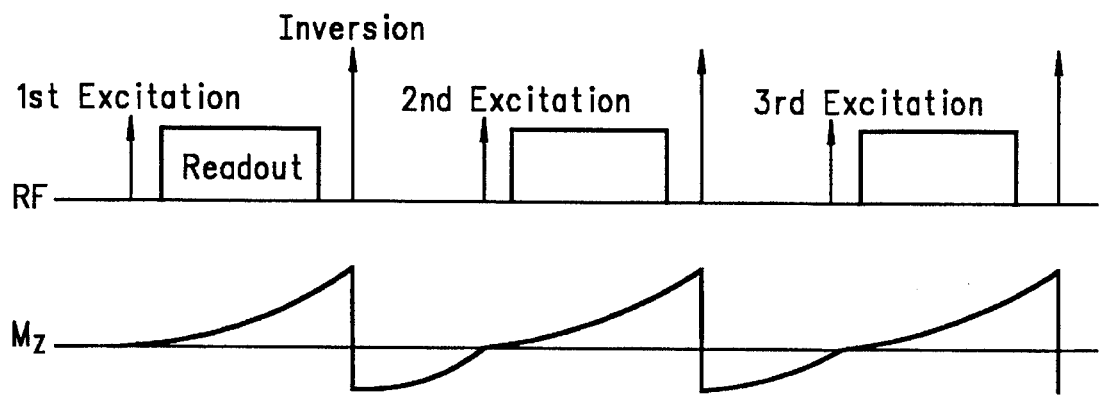
FIG. 8 illustrates a multiple pulse sequence for signal read-out in accordance with the invention.

In addition, another method of multi-tip acquisition could be to use a null-readout-180-new null-readout, etc. sequence, as displayed in FIG. 8. This sequence would continually recreate null points and image them. Although the nulling would be imperfect, it still should be good enough for image acquisition. Again, the lower frequency k-space data would be acquired at the better null points.

Figures 9A, 9B:
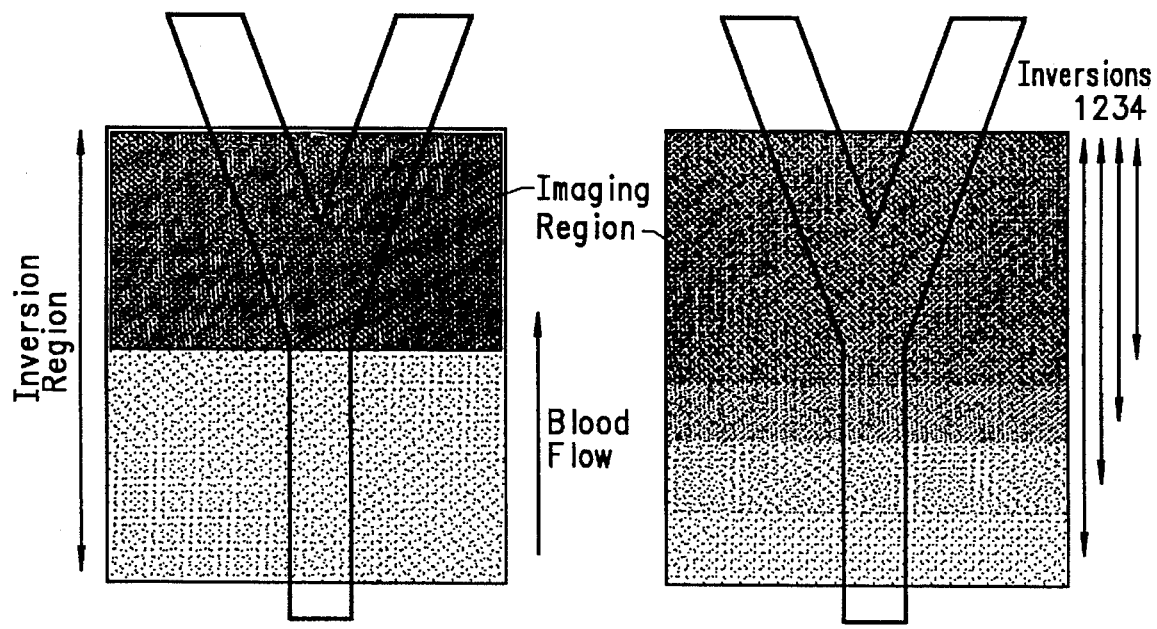
FIGS. 9A, 9B illustrate the use of multiple selective inversions in a read-out sequence.

A potential improvement to MIR to increase the signal of the blood would be to make the inversions somewhat selective. Currently, the steady-state magnetization of the blood is reduced by the nonselective 180s. This may invert blood which will later flow into the imaging region, reducing its signal. The inversions could be made somewhat selective, inverting a region upstream of the imaging region as well as the imaging region, but not including the farther downstream blood that would comprise signal, for the next frame of data to be acquired. This is displayed in FIG. 9A. In fact, as detailed in FIG. 9B, the inversions could even move inward, minimally disturbing the blood that will flow into the imaging region for the next frame of data. This would avoid the steady-state reduction in the blood signal.

Perfusion imaging is another application of this technique, in which a slab is nulled with a long in-flow time, and a relatively thick slice (3 mm–15 mm) imaged. Slow flowing blood moves into the null static tissue region and is seen when reading out at the null point. This technique has been demonstrated in the brain, and would be most effective with long readout times. In this method, blood moving into the imaging slab from out of the imaging slab would be imaged. So it would image flow parallel to the imaging slice select direction.

Another potential method to image perfusion could be to create a spatial grid of longitudinal magnetization using a technique such as SPAMM. See Axel et al., Radiology, 172, 349–350 (1989). This would be used to make a spatially alternating $M_z$ varying between 0 and the original $M_z$. The multiple inversion recovery sequence could be performed on the grid, and the magnetization imaged after a long inflow time. In this case, blood moving in the imaging plane would be seen as moving in between the lines of the SPAMM grid. This is because the signal in between the lines of the SPAMM grid would be zero unless blood moved into them.

There have been described several embodiments of Multiple Inversion Recovery imaging in accordance with the invention. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

What is claimed is:

1. A method of multiple inversion recovery imaging signal detection comprising the steps of
    a) placing an object to be imaged in a magnetic field,
    b) applying RF excitation to saturate static nuclei spins,
    c) applying at least four spin inversion pulses to null nuclei in static material having different spin-lattice relaxation times ($T_1$); and
    d) applying at least one read-out pulse and detecting emitted magnetic resonance signals.

2. The method as defined by claim 1 wherein in step c) said spin inversion pulses are spaced in time to substantially reduce the longitudinal magnetization of the different $T_1$ species present.

3. The method as defined by claim 1 wherein step b) includes applying a sequence of saturation pulses with adjacent pulses being separated by a dephasing gradient to avoid refocusing coherence.

4. The method as defined by claim 3 wherein said sequence of saturation pulses includes five pulses.

5. The method as defined by claim 3 wherein step d) includes applying a plurality of RF read-out pulses with the low spatial frequency data being acquired near the null point, the detecting of emitted signals occurring after each RF read-out pulse.

6. The method as defined by claim 1 wherein step d) includes applying a plurality of RF read-out pulses with the low spatial frequency data being acquired near the null point, the detecting of emitted signals occurring after each RF read-out pulse.

7. Apparatus for multiple inversion recovery imaging signal detection comprising
    a) means applying a magnetic field through an object to be imaged,
    b) means applying RF excitation to saturate static nuclei spins,
    c) means applying at least four spin inversion pulses to null nuclei in static material having different spin-lattice relaxation times ($T_1$); and
    d) means detecting emitted magnetic resonance signals.

8. Apparatus as defined by claim 7 wherein said means for applying at least four magnetic inversion pulses applies pulses spaced in time to substantially reduce the longitudinal magnetization at the various $T_1$ species.

9. Apparatus as defined by claim 7 wherein said means for applying RF excitation applies a sequence of saturation pulses with adjacent pulses being separated by a dephasing gradient to avoid refocusing coherence.

10. Apparatus as defined by claim 9 wherein said sequence of saturation pulses includes five pulses.

11. Apparatus as defined by claim 9 wherein said means for detecting emitted signals applies a plurality of RF read-out pulses with the low spatial frequency data acquired near the null point, the detecting of emitted signals occurring after each RF read-out pulse.

12. Apparatus as defined by claim 9 wherein said means for detecting emitted signals applies a plurality of RF read-out pulses with the low spatial frequency data acquired near the null point, the detecting of emitted signals occurring after each RF read-out pulse.

* * * * *